United States Patent
Khosla et al.

(10) Patent No.: US 11,154,308 B2
(45) Date of Patent: Oct. 26, 2021

(54) DRILL ASSEMBLY FOR PREPARATION OF SURGICAL SITES

(71) Applicant: Arthrex, Inc., Naples, FL (US)

(72) Inventors: Rudraksh Khosla, Naples, FL (US); Michael Alan Knight, Naples, FL (US); John David Paterson, Naples, FL (US); Alexander Emmanuel Rodriguez, Weston, FL (US); Tyler Clevett, Bonita Springs, FL (US)

(73) Assignee: ARTHREX, INC., Naples, FL (US)

( * ) Notice: Subject to any disclaimer, the term of this patent is extended or adjusted under 35 U.S.C. 154(b) by 195 days.

(21) Appl. No.: 16/540,144

(22) Filed: Aug. 14, 2019

(65) Prior Publication Data

US 2021/0045754 A1 Feb. 18, 2021

(51) Int. Cl.
*A61B 17/00* (2006.01)
*A61B 17/16* (2006.01)
*A61B 90/00* (2016.01)

(52) U.S. Cl.
CPC .......... *A61B 17/1633* (2013.01); *A61B 90/03* (2016.02); *A61B 2017/00407* (2013.01); *A61B 2090/034* (2016.02)

(58) Field of Classification Search
CPC combination set(s) only.
See application file for complete search history.

(56) References Cited

U.S. PATENT DOCUMENTS

| | | | |
|---|---|---|---|
| 7,141,074 B2 | 11/2006 | Fanger et al. | |
| 7,163,542 B2 | 1/2007 | Ryan | |
| 9,839,436 B2 | 12/2017 | Kehres et al. | |
| 10,314,598 B2 | 6/2019 | Knape et al. | |
| 2007/0282344 A1 | 12/2007 | Yedlicka et al. | |
| 2012/0010659 A1* | 1/2012 | Angert | A61B 17/7064 606/247 |
| 2013/0171585 A1 | 7/2013 | Huang | |
| 2018/0161124 A1 | 6/2018 | Huwais | |
| 2018/0250020 A1 | 9/2018 | Carusillo | |

FOREIGN PATENT DOCUMENTS

DE 3800482 7/1989
WO 2019035096 2/2019

OTHER PUBLICATIONS

International Search Report & Written Opinion for International Patent Application No. PCT/US2020/045866completed Nov. 5, 2020.

* cited by examiner

*Primary Examiner* — Sameh R Boles
(74) *Attorney, Agent, or Firm* — Carlson, Gaskey & Olds, P.C.

(57) ABSTRACT

This disclosure relates to a drill assembly and method for preparing a surgical site. The drill assembly disclosed herein may be utilized for removing bone prior to positioning a graft and/or implant at a surgical site.

13 Claims, 6 Drawing Sheets

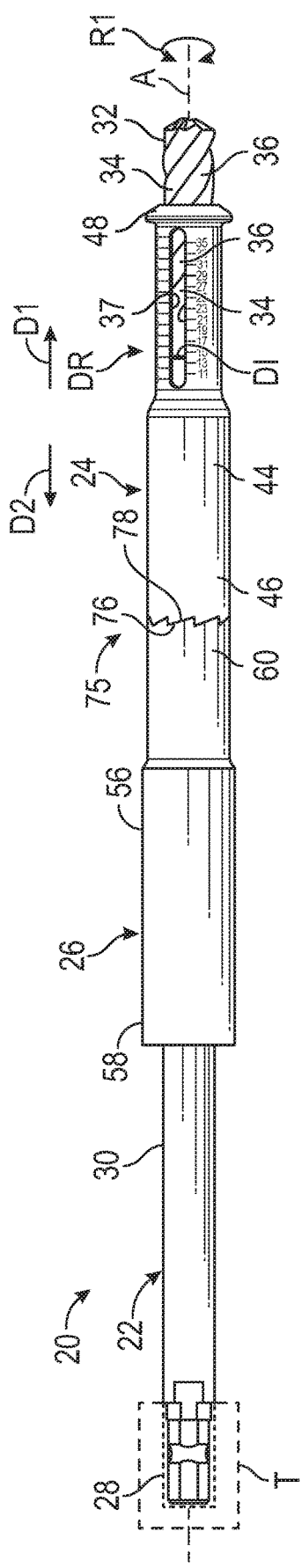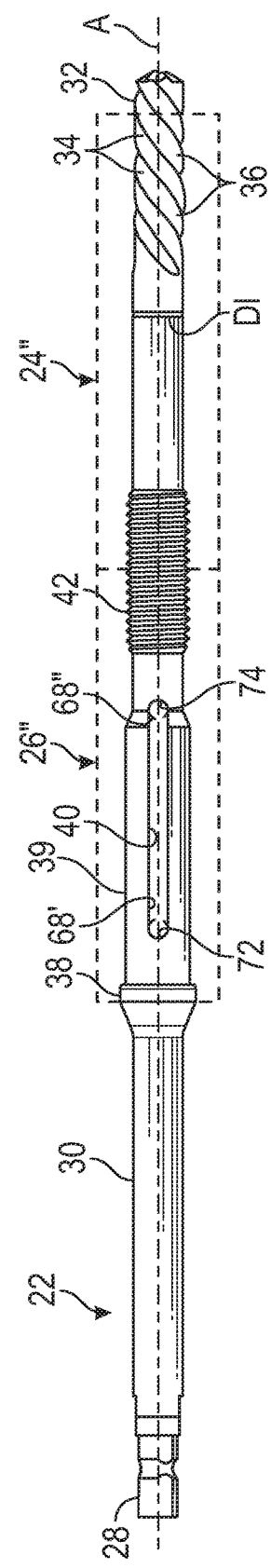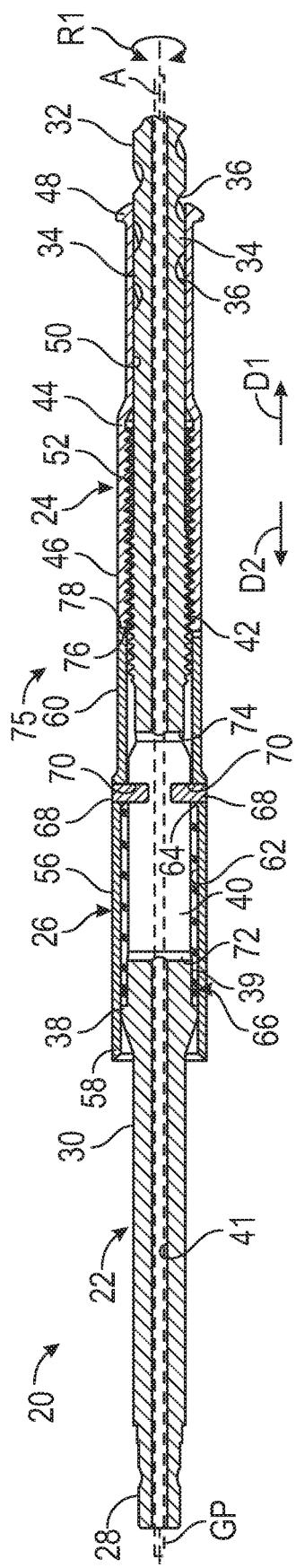
FIG. 2
FIG. 3
FIG. 4

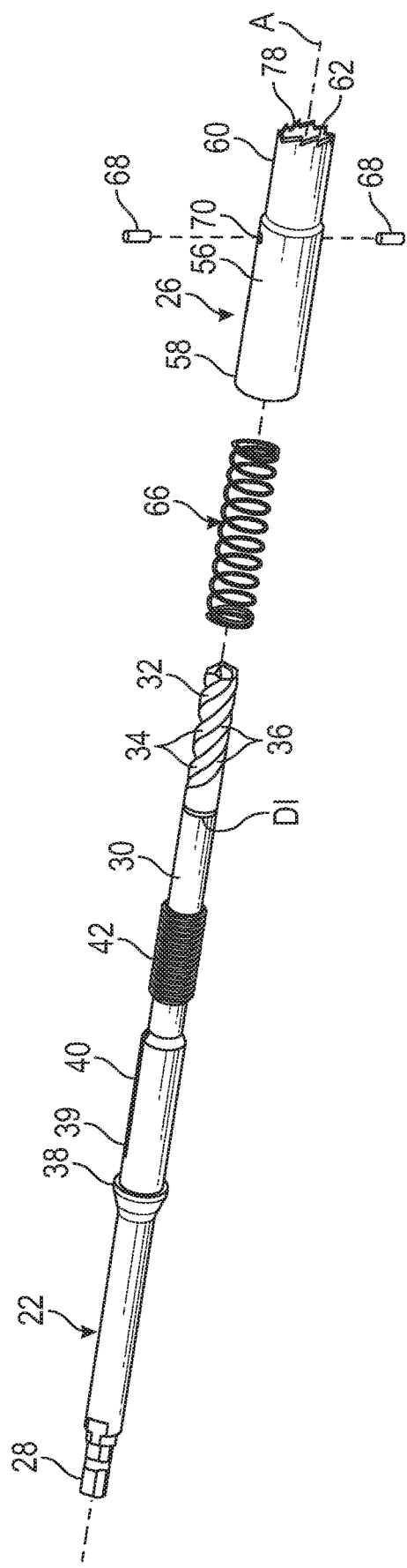
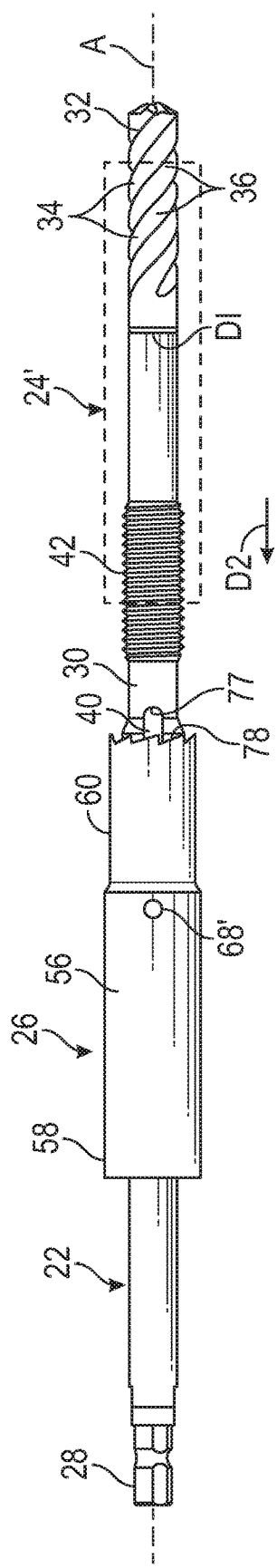
FIG. 5
FIG. 6

DRILL ASSEMBLY FOR PREPARATION OF SURGICAL SITES

BACKGROUND

This disclosure relates to surgical devices and methods for preparing surgical sites, such as forming recesses in bone.

Many bones of the human musculoskeletal system include articular surfaces. The articular surfaces articulate relative to other bones to facilitate different types and degrees of joint movement. The articular surfaces can erode (i.e., experience bone loss) over time due to repeated use or wear or can fracture as a result of a traumatic impact. These types of bone defects can cause joint instability and pain.

Bone deficiencies may occur along the articular surfaces of the glenoid bone. Some techniques utilize a bone graft and/or implant to a fill defect in the glenoid bone. A drill may be utilized to form a recess in the bone dimensioned to receive a portion of the implant.

SUMMARY

This disclosure relates to surgical devices and methods. The surgical device may be used during methods for preparing surgical sites, including repairing bone defects. The surgical device described herein may be utilized to form a recess or otherwise shape a surface at a surgical site.

A drill assembly for preparation of a surgical site according to an embodiment of the present disclosure includes, inter alia, a drill shaft including one or more cutting surfaces, and a depth collar dimensioned to at least partially cover the one or more cutting surfaces. The depth collar includes a first set of teeth, a ratcheting sleeve including a second set of teeth, and, when the first set of teeth and the second set of teeth are engaged together, the ratcheting sleeve limits movement of the depth collar.

A drill assembly for preparation of a surgical site according to an embodiment of the present disclosure includes, inter alia, a drill shaft including one or more cutting surfaces, a depth collar movable along the one or more cutting surfaces in response to relative rotation between the depth collar and the drill shaft, the depth collar including a distal end portion dimensioned to contact bone adjacent to the one or more cutting surfaces, and a ratcheting sleeve moveable along the drill shaft between a first position and a second, different position relative to a longitudinal axis of the drill shaft. The ratcheting sleeve is spaced apart from the depth collar in the first position and is engaged with the depth collar in the second position such that the ratcheting sleeve limits relative rotation between the depth collar and the drill shaft.

A method of preparing a surgical site according to an embodiment of the present disclosure includes, inter alia, moving a depth collar relative to a drill shaft such that the depth collar at least partially covers one or more cutting surfaces of the drill shaft, moving a ratcheting sleeve along the drill shaft to engage the depth collar such that the ratcheting sleeve limits relative rotation between the depth collar and the drill shaft, and rotating the drill shaft to remove tissue at a surgical site.

BRIEF DESCRIPTION OF THE DRAWINGS

FIG. 2 illustrates a side view of the assembly of FIG. 1.

FIG. 3 illustrates a side view of a drill shaft.

FIG. 4 illustrates a sectional view taken along a length of the assembly of FIG. 2.

FIG. 5 illustrates an exploded view of selected components of the assembly of FIG. 1.

FIG. 6 illustrates a side view of a ratcheting sleeve positioned relative to the drill shaft of FIG. 3.

DETAILED DESCRIPTION

Figure 1:
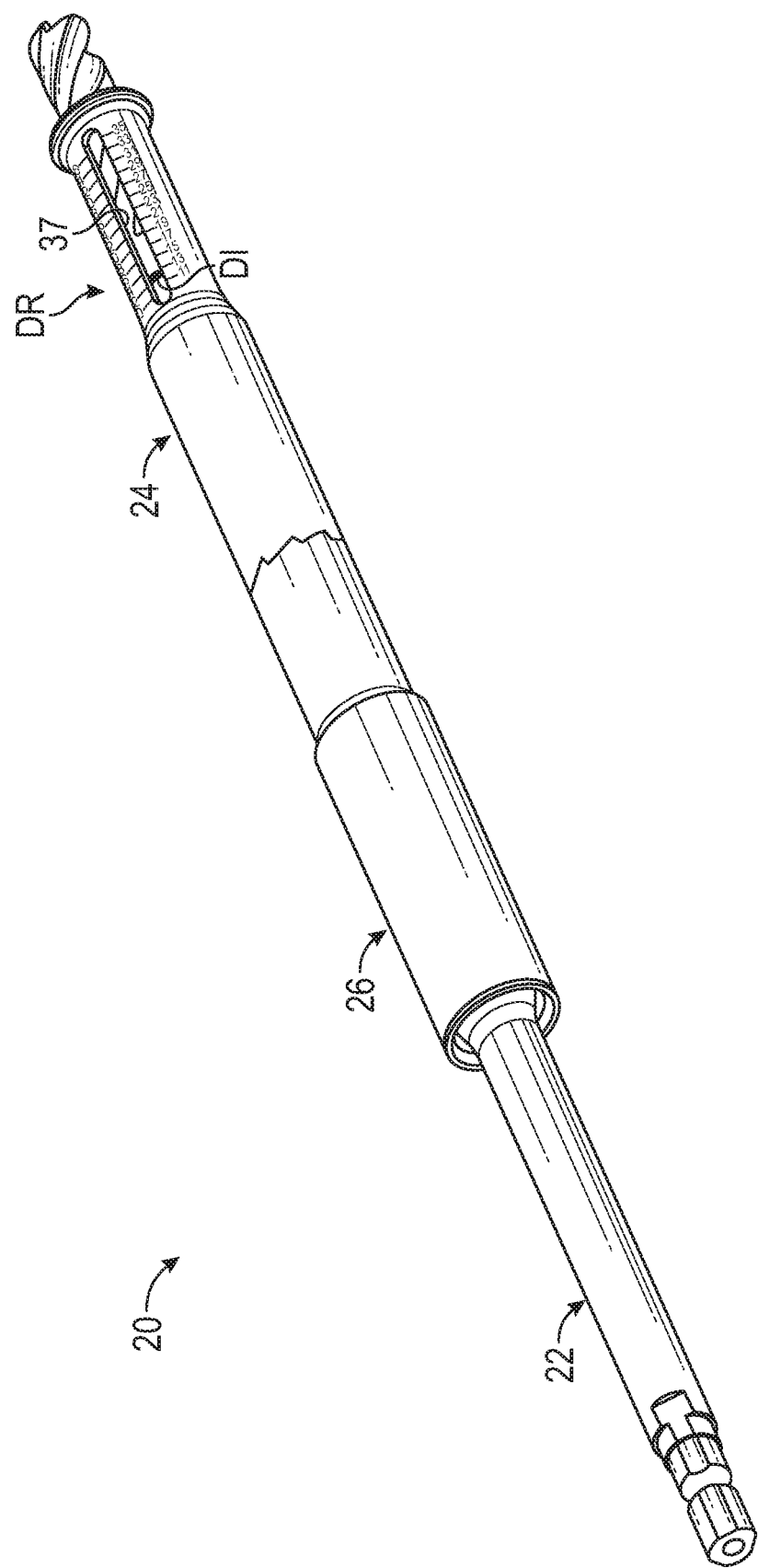
FIG. 1 illustrates a perspective view of an exemplary drill assembly for preparing a surgical site.
Figure 7:
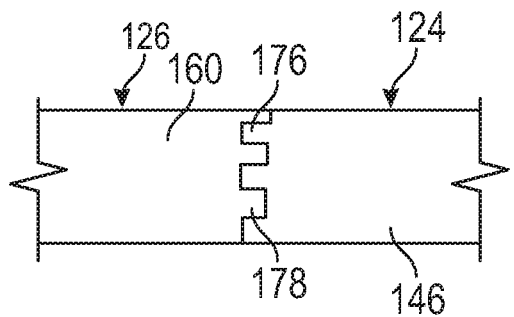
FIG. 7 illustrates a depth collar and a ratcheting sleeve according to another embodiment.

This disclosure relates to surgical devices and methods for preparing a surgical site, including repairing bone defects. The device described herein may be capable of dimensioning or otherwise preparing a defect surface at a surgical site, including removing bone or other tissue to form a hole or recess at a selected depth.

A drill assembly for preparation of a surgical site according to an embodiment of the present disclosure includes, inter alia, a drill shaft including one or more cutting surfaces, and a depth collar dimensioned to at least partially cover the one or more cutting surfaces. The depth collar includes a first set of teeth, a ratcheting sleeve including a second set of teeth, and, when the first set of teeth and the second set of teeth are engaged together, the ratcheting sleeve limits movement of the depth collar.

In a further embodiment, the drill shaft includes an intermediate portion between a shank portion and a drill body portion. The drill body portion includes the one or more cutting surfaces, the depth collar includes first threading along a first passageway dimensioned to at least partially receive the intermediate portion, and the intermediate portion includes second threading dimensioned to engage with the first threading such that relative rotation between the depth collar and the intermediate portion causes the depth collar to move along a longitudinal axis of the drill shaft.

In a further embodiment, the depth collar includes a first set of teeth, and the ratcheting sleeve includes a second set of teeth dimensioned to mate with the first set of teeth to oppose relative rotation between the depth collar and the drill shaft.

In a further embodiment, the first set of teeth extend axially from a proximal end portion of the depth collar relative to the longitudinal axis, and the second set of teeth extend axially from a distal end portion of the ratcheting sleeve relative to the longitudinal axis.

In a further embodiment, a spring member biases the second set of teeth towards the first set of teeth.

In a further embodiment, the depth collar includes a viewing window at least partially axially aligned with the one or more cutting surfaces relative to the longitudinal axis.

In a further embodiment, a spring member biases the ratcheting sleeve towards the depth collar in an installed position.

In a further embodiment, the drill shaft includes an intermediate portion between a shank portion and a drill body portion. The drill body portion comprising the one or more cutting surfaces. The intermediate portion includes a first shoulder. The ratcheting sleeve includes a second passageway at least partially receiving the intermediate portion, and the ratchet sleeve includes a second shoulder along the second passageway. The spring member is compressible between the first shoulder and the second shoulder in response to moving the ratcheting sleeve in a direction away from the drill body portion.

In a further embodiment of any of the foregoing embodiments, the intermediate portion includes a slot, and a retention pin is mechanically attached to the ratcheting sleeve such that the retention pin is at least partially received in the slot.

In a further embodiment, the retention pin extends inwardly from a sidewall of the ratcheting sleeve bounding the second passageway such that the retention pin limits relative rotation between the ratcheting sleeve and the drill shaft.

In a further embodiment, the drill shaft includes a shaft passageway extending along a longitudinal axis between the shank portion and the drill body portion such that the shaft passageway intersects the slot.

A drill assembly for preparation of a surgical site according to an embodiment of the present disclosure includes, inter alia, a drill shaft including one or more cutting surfaces, a depth collar movable along the one or more cutting surfaces in response to relative rotation between the depth collar and the drill shaft, the depth collar including a distal end portion dimensioned to contact bone adjacent to the one or more cutting surfaces, and a ratcheting sleeve moveable along the drill shaft between a first position and a second, different position relative to a longitudinal axis of the drill shaft. The ratcheting sleeve is spaced apart from the depth collar in the first position and is engaged with the depth collar in the second position such that the ratcheting sleeve limits relative rotation between the depth collar and the drill shaft.

In a further embodiment, the depth collar includes a first set of teeth, and the ratcheting sleeve includes a second set of teeth dimensioned to mate with the first set of teeth in the second position.

In a further embodiment, a retention pin limits relative rotation between the ratcheting sleeve and the drill shaft.

A method of preparing a surgical site according to an embodiment of the present disclosure includes, inter alia, moving a depth collar relative to a drill shaft such that the depth collar at least partially covers one or more cutting surfaces of the drill shaft, moving a ratcheting sleeve along the drill shaft to engage the depth collar such that the ratcheting sleeve limits relative rotation between the depth collar and the drill shaft, and rotating the drill shaft to remove tissue at a surgical site.

In a further embodiment, the step of moving the depth collar includes rotating the depth collar and drill shaft relative to each other such that first threading along the depth collar engages second threading along the drill shaft.

In a further embodiment, the step of moving the ratcheting sleeve along the drill shaft includes causing a first set of teeth along a proximal end portion of the depth collar to mesh with a second set of teeth along a distal end portion of the ratcheting sleeve.

In a further embodiment, the step of moving the depth collar includes at least partially aligning the one or more cutting surfaces and a viewing window along the depth collar relative to a longitudinal axis of the drill shaft.

In a further embodiment, the method includes moving the drill shaft along a guide pin situated at the surgical site.

In a further embodiment, the method includes moving the ratcheting sleeve away from the depth collar to cause a spring member to at least partially compress. The step of moving the ratcheting sleeve along the drill shaft includes at least partially decompressing the spring member to bias the ratcheting sleeve against the depth collar.

FIGS. 1-7 illustrate an exemplary cutting or drill assembly 20 that can be utilized for various surgical procedures, such as for preparation of a surgical site. For example, the assembly 20 may be utilized in a shoulder reconstruction to remove bone along an articulating surface of a glenoid or humeral head. The bone may be removed adjacent to a defect in the articulating surface.

Referring to FIGS. 1-2, the assembly 20 includes an elongated drill shaft 22, a depth collar (or sleeve) 24, and a ratcheting sleeve 26. The drill shaft 22 can be utilized to form a recess in tissue along a surgical site, such as a bone hole. The depth collar 24 provides a variable depth feature and is dimensioned to set a depth of the hole or recess formed in the surgical site. The ratcheting sleeve 26 cooperates with the depth collar 24 to limit or otherwise oppose relative rotation or movement between the depth collar 24 and drill shaft 22.

The drill assembly 20 includes a depth ruler DR and a depth indicator DI moveable relative to each other to limit a depth of the hole or recess formed in the surgical site. In the illustrative embodiment of FIGS. 1-2, the drill shaft 22 includes the depth indicator DI, and the depth collar 24 includes the depth ruler DR. Of course, an opposite configuration is also contemplated in which the drill shaft 22 includes the depth ruler DR, and the depth collar 24 includes the depth indicator DI. The depth indicator DI is aligned with a selected position along the depth ruler DR in response to translating or otherwise moving the depth collar 24 relative to the drill shaft 22.

The depth ruler DR can correspond to a range of depths of a hole or recess to be formed in the surgical site. The depth ruler DR can range between approximately 10 mm and approximately 36 mm in 1 mm increments as illustrated in FIGS. 1-2, for example. It should be appreciated that a minimum value of the depth ruler DR can be lesser or greater than 10 mm, such as approximately 5 or 15 mm, and a maximum depth of the depth ruler DR can be lesser or greater than 36 mm, such as approximately 30 or 37 mm.

Referring to FIGS. 3-4, with continuing reference to FIG. 2, the drill shaft 22 extends along a longitudinal axis A, and includes a shank portion 28, an intermediate portion 30, and a drill body portion 32. The shank portion 28 and drill body portion 32 include proximal and distal ends of the drill shaft 22, respectively. The shank portion 28 can be dimensioned to cooperate with tooling T (shown in dashed lines in FIG. 2 for illustrative purposes) to rotate or otherwise drive the shaft 22. For example, the shank portion 28 can be mounted to a chuck of the tooling T. The intermediate portion 30 extends along the longitudinal axis A between the shank portion 28 and drill body portion 32. The drill body portion 32 includes one or more cutting surfaces 34 spaced between one or more grooves or flutes 36. The depth indicator DI can be proximal to the drill body portion 32.

The assembly 20 includes at least one elongated viewing window 37 (FIGS. 1-2) along a sidewall of the depth collar 24. The viewing window 37 is at least partially axially aligned with the cutting surfaces 34 and depth indicator DI relative to the longitudinal axis A, as illustrated in FIG. 2.

The drill shaft 22 includes a first annular shoulder 38 that extends about an outer periphery 39 of the intermediate portion 30. The intermediate portion 30 includes an elongated slot 40 dimensioned to extend along the longitudinal axis A between opposed sidewalls along the outer periphery 39 of the intermediate portion 30. The intermediate portion 30 includes a first threading 42 about the outer periphery 39. The first threading 42 is between the slot 40 and drill body portion 32.

Figure 10:
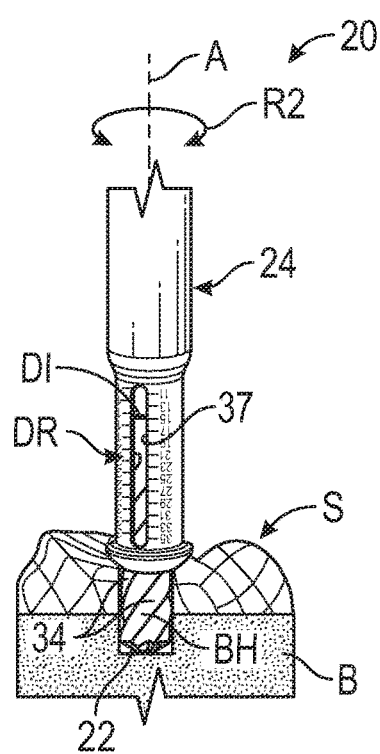
FIG. 10 illustrates the instrument of FIG. 1 situated at another position relative to the surgical site of FIG. 9.

Referring to FIG. 4, with continuing reference to FIGS. 2-3, the depth collar 24 is disposed about the drill body portion 32 and is dimensioned to at least partially cover the cutting surface 34 for one or more positions of the depth collar 24 relative to the longitudinal axis A. The depth collar 24 includes a main body 44 that extends between a proximal end portion 46 and a distal end portion 48 opposed to the proximal end portion 46. The distal end portion 48 is dimensioned to contact tissue such as bone adjacent to the cutting surfaces 34, as illustrated in FIG. 10.

The depth collar 24 includes a first passageway 50 dimensioned to at least partially receive the drill body portion 32 and intermediate portion 30 of the drill shaft 22. The depth collar 24 includes second threading 52 along the first passageway 50. The depth collar 24 is moveable in a direction D1 towards a terminal end of the drill body portion 32, and is moveable in a direction D2 towards a terminal end of the shank portion 28 (see FIGS. 2 and 4). The first threading 42 along the drill shaft 22 is dimensioned to engage with the second threading 52 such that relative rotation between the depth collar 24 and the intermediate portion 30 in a rotational direction R1 (e.g., clockwise or counterclockwise) causes the depth collar 24 to translate or otherwise move in the direction D1 or direction D2 along the longitudinal axis A of the drill shaft 22. The depth collar 24 is moveable along the one or more cutting surfaces 34 in response to relative rotation between the depth collar 24 and the drill shaft 22. Relative movement between the drill shaft 22 and depth collar 24 causes relative movement between the depth indicator DI and depth ruler DR.

The drill shaft 22 can include a shaft passageway 41 extending along the longitudinal axis A between the shank portion 28 and drill body portion 32. The passageway 41 can be dimensioned to slidably receive a guide pin GP (shown in dashed lines for illustrative purposes). The passageway 41 can be dimensioned such that the passageway 41 intersects the slot 40, as illustrated in FIG. 4.

Referring to FIGS. 4-5, with continuing reference to FIG. 2, the ratcheting sleeve 26 includes a main body 56 that extends between a proximal end portion 58 and a distal end portion 60. The ratcheting sleeve 26 includes a second passageway 62 dimensioned to at least partially receive the intermediate portion 30 of the drill shaft 22. The ratcheting sleeve 26 includes a second annular shoulder 64 (FIG. 4) along the second passageway 62.

The assembly 20 includes a spring member 66 disposed along the outer periphery 39 of the intermediate portion 30. The spring member 66 is dimensioned to bias the ratcheting sleeve 26 towards the depth collar 24 in an installed position. The spring member 66 can be a coil spring as illustrated in FIGS. 4-5, for example. Other spring configurations can be utilized, such as torsion springs and wave springs. The spring member 66 is trapped between the first and second shoulders 38, 64 in the installed position, as illustrated in FIG. 4. The spring member 66 is dimensioned to bias the ratcheting sleeve 26 in the direction D1 towards the drill body portion 32. The spring member 66 is at least partially compressible between the first and second shoulders 38, 64 in response to axially moving the ratcheting sleeve 26 in the direction D2 away from the drill body portion 32 and/or depth collar 24 relative to the longitudinal axis A, as illustrated in FIG. 4 (see also FIG. 6).

The drill assembly 20 includes at least one fastener or retention pin 68 mechanically attached to the ratcheting sleeve 26. Each retention pin 68 is at least partially received in the slot 40. In the illustrative embodiment of FIG. 4, the assembly 20 includes a pair of retention pins 68 each extending inwardly from a sidewall of the ratcheting sleeve 26 bounding the passageway 62. Each retention pin 68 is dimensioned to limit relative rotation and axial movement between the ratcheting sleeve 26 and drill shaft 22. The retention pins 68 are dimensioned to translate or axially move relative to the longitudinal axis A in the slot 40 between opposed end faces 72, 74 (FIGS. 3-4) bounding the slot 40.

In the illustrative embodiment of FIG. 4, the slot 40 extends between the opposed sidewalls of the intermediate portion 30 such that the slot 40 receives a pair of the retention pins 68. In other embodiments, the drill shaft 22 includes separate and distinct slots 40 along the outer periphery 39 of the intermediate portion 30 with the slots 40 dimensioned to receive a respective retention pin 68.

The ratcheting sleeve 26 is moveable along the drill shaft 22 between a first or fully retracted position (e.g., FIG. 6, with depth collar 24' shown in dashed lines for illustrative purposes), and a second, different position (e.g., FIG. 3, with collar 24" and sleeve 26" shown in dashed lines for illustrative purposes). FIGS. 2 and 4 illustrate the ratcheting sleeve 26 in an intermediate position relative to the longitudinal axis A of the drill shaft 22. The ratcheting sleeve 26 is spaced apart from the depth collar 24' in the first position. The ratcheting sleeve 26 is engaged with the depth collar 24" in the second position and can be engaged with the depth collar 24 in the intermediate position such that the ratcheting sleeve 26 limits relative rotation and axial movement between the depth collar 24, 24" and drill shaft 22.

The retention pins 68 are dimensioned to abut against the first one of the end faces 72 in the first position and are dimensioned to abut against another one of the end faces 74 in the second position to limit axial movement of the ratcheting sleeve 26 relative to the drill shaft 22 (first and second positions indicated at 68' and 68" in dashed lines in FIG. 3 for illustrative purposes). FIG. 6 illustrates retention pin 68' with the ratcheting sleeve 26 moved in the direction D2 to the first position.

Each retention pin 68 is dimensioned to engage with lateral surfaces of the slot 40 to limit relative rotation between the ratcheting sleeve 26 and drill shaft 22. The ratcheting sleeve 26 is disposed about the intermediate portion 30 of the drill shaft 22 such that the ratcheting sleeve 26 selectively limits relative rotation between the depth collar 24 and drill shaft 22.

The assembly 20 includes an anti-rotation mechanism 75 (FIGS. 2 and 4) operable to limit relative rotation between drill shaft 22 and depth collar 24. In the illustrated embodiment of FIGS. 2 and 4, the anti-rotation mechanism 75 includes a first set of teeth 76 dimensioned to engage and mesh with a second set of teeth 78. The depth collar 24 can include the first set of teeth 76, and the ratcheting sleeve 26 can include the second set of teeth 78 (see also FIGS. 5-6). The first set of teeth 76 extend axially from the proximal end portion 46 of the depth collar 24, and the second set of teeth 78 extend axially from the distal end portion 60 of the ratcheting sleeve 26 relative to the longitudinal axis A. In the illustrated embodiment of FIG. 2, the first and second sets of teeth 76, 78 have a generally sawtooth geometry. It should be appreciated that other geometries of the teeth 76, 78 can be utilized, such as a generally rectangular profile as illustrated by teeth 176, 178 of FIG. 7.

The first set of teeth 76 are dimensioned to mate with the second set of teeth 78 to oppose relative rotation between the depth collar 24 and drill shaft 22. The spring member 66 is dimensioned to bias the second set of teeth 78 in the direction D1 towards the first set of teeth 76. The second set of teeth 78 are dimensioned to mate with the first set of teeth 76 in the position(s) in which the depth collar 24 abuts against the ratcheting sleeve 26, as illustrated in FIGS. 2-4. The teeth 76, 78 can be disengaged by holding the depth collar 24 and rotating the ratcheting sleeve 26 in a direction (e.g., clockwise or counterclockwise) utilized to move the depth collar 24 away from the drill body portion 32.

Figure 8:
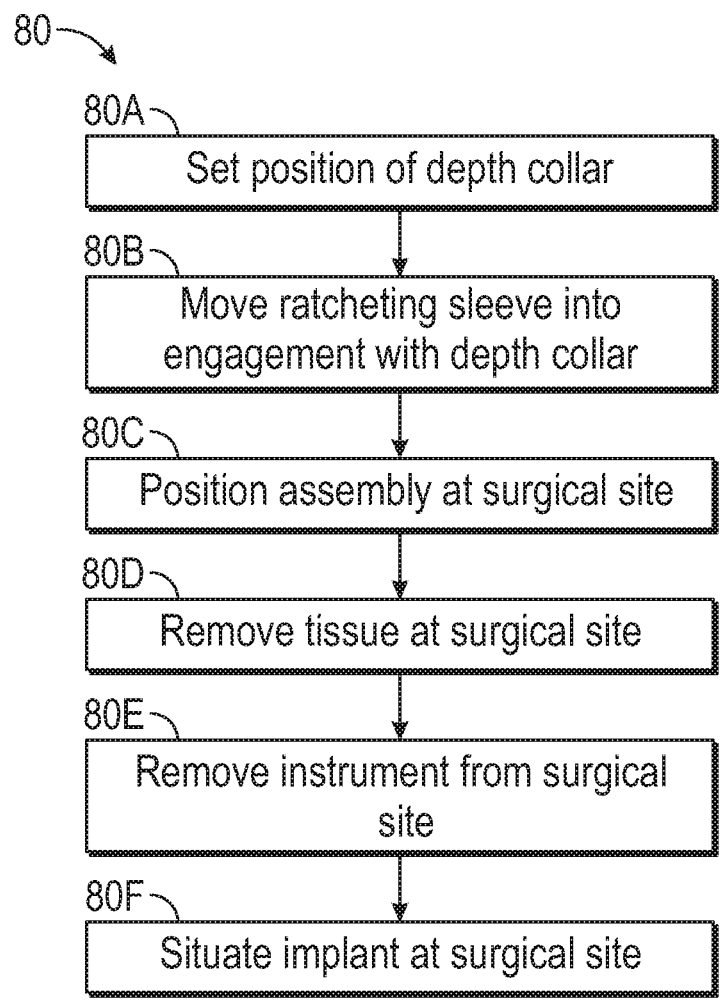
FIG. 8 illustrates an exemplary method for preparing a surgical site.

An exemplary method of use will now be described. Referring to FIG. 8, an exemplary method in a flowchart 80 for preparing a surgical site is shown. Reference is made to the drill assembly 20 of FIGS. 9-10 for illustrative purposes. In should be appreciated that one or more of the steps of method 80 may be performed with the reaming assembly 20. The method 80 can be utilized to forming a recess or hole at a surgical site, such as a bone hole in an articulating surface of a glenoid. The bone may be removed adjacent to a defect in the articulating surface. Fewer or additional steps than are recited below could be performed within the scope of this disclosure, and the recited order of steps is not intended to limit this disclosure.

Figure 9:
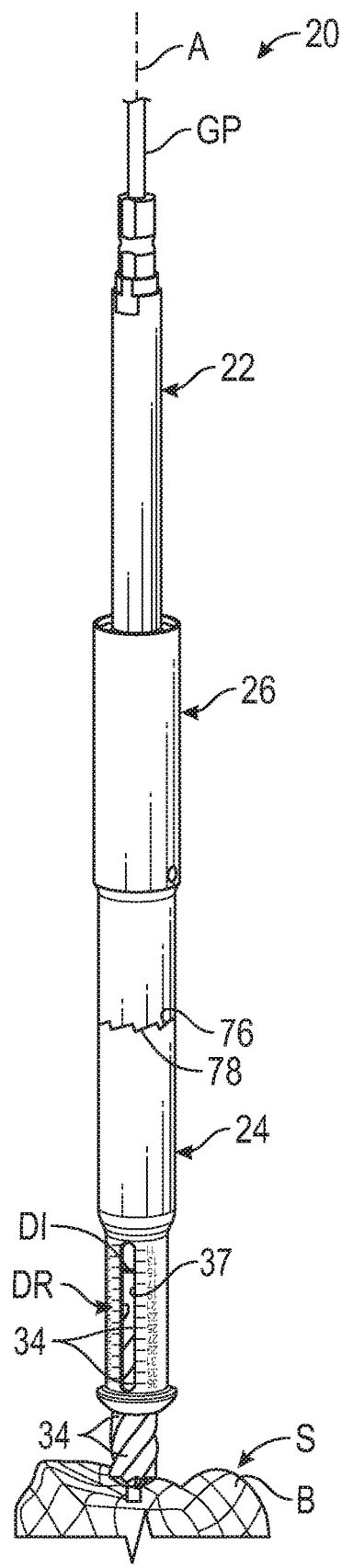
FIG. 9 illustrates the instrument of FIG. 1 situated at a surgical site.

At step 80A, a position of the depth collar 24 is set corresponding to a depth of a recess or hole to be formed in a surgical site S (FIGS. 9-10). Step 80A can include moving the depth collar 24 relative to the drill shaft 22 such that the depth collar 24 at least partially covers one or more cutting surfaces 34 of the drill shaft 22. Step 80A includes at least partially aligning the cutting surfaces 34 and the viewing window 37 relative to the longitudinal axis A. The depth collar 24 is moved to align the depth indicator DI with a selected value along the depth ruler DR. Step 80A can include holding the drill shaft 22 and rotating the depth collar 24 about the drill shaft 22 to cause the relative movement between the depth indicator DI and depth ruler DR. The surgeon can verify the position of the depth indicator DI through the viewing window 37. Step 80A can include, prior to moving the depth collar 24 to a position corresponding to the selected depth, disengaging the teeth 76, 78 and moving the ratcheting sleeve 26 away from the depth collar 24 to cause the spring member 66 to at least partially compress, as illustrated in FIG. 6.

At step 80B, the ratcheting sleeve 26 is moved along the drill shaft 22 to engage the depth collar 24 such that the ratcheting sleeve 26 limits relative rotation and axial movement between the depth collar 24 and drill shaft 22. Step 80B can include moving the ratcheting sleeve 26 along the drill shaft 22 to at least partially decompress the spring member 66 such that the spring member 66 biases the ratcheting sleeve 26 against the depth collar 24, as illustrated in FIG. 4. Step 80B can include rotating the depth collar 24 and drill shaft 22 in the rotational direction R1 relative to each other such that the threading 42 along the drill shaft 22 engages the threading 52 along the depth collar 24 to move the depth collar 24 along the longitudinal axis A, as illustrated in FIG. 4. Step 80B can include causing the teeth 76 along the depth collar 24 to mesh with the teeth 78 along the ratcheting sleeve 26, as illustrated in FIGS. 2 and 4.

Referring to FIG. 9, with continuing reference to FIG. 8, at step 80C the assembly 20 is positioned at the surgical site S. In embodiments, the surgical site S is a glenoid bone B of a shoulder joint. However, the method could be performed in various other tissue within the scope of this disclosure. In other words, this disclosure is in no way limited to forming a recess or hole in bone along the glenoid. Step 80C can include positioning the assembly 20 relative to a guide pin GP situated in bone B at the surgical site S. The guide pin GP may be positioned at least partially in the passageway 41 of the drive shaft 22, as illustrated in FIG. 4. Step 80C can include moving the drill shaft 22 along the guide pin GP and into contact with the bone B.

Referring to FIG. 10, with continuing reference to FIG. 8, at step 80D a portion of the bone B or other tissue is removed at the surgical site S to form a recess or bone hole BH dimensioned to the selected depth corresponding to a position of the depth indicator DI relative to the depth ruler DR. Step 80D can include rotating the drill shaft 22 in a direction R2 about the longitudinal axis A to form the bone hole BH. The instrument 20 can be removed from the surgical site S at step 80E.

Figure 11:
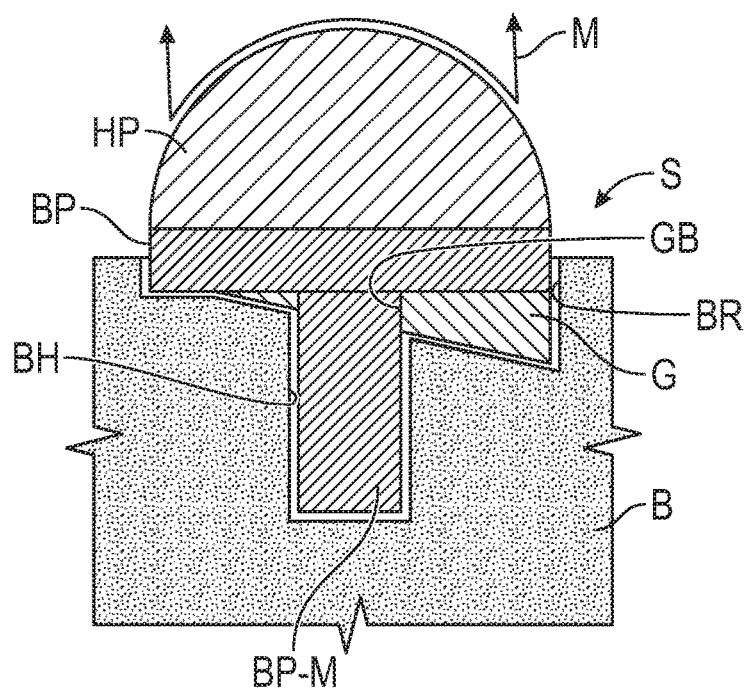
FIG. 11 schematically illustrates an implant and graft positioned at a surgical site.
Figure 12:
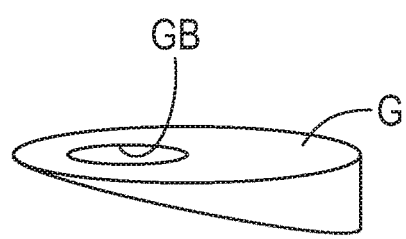
FIG. 12 illustrates an isolated perspective view of the graft of FIG. 11.

Referring to FIG. 11, with continuing reference to FIG. 8, at step 80F the surgeon can position an implant such as a bone plate BP at the surgical site S. Step 80F can include placing or otherwise securing a graft G to the bone plate BP. The graft G can have a generally wedge-shaped geometry as illustrated by FIGS. 11-12, for example. The graft G can be oriented relative to a defect in the bone B.

The bone plate BP can include an anchoring member BP-M. The anchoring member BP-M can serve as a central post of the bone plate BP, for example. The anchoring member BP-M can be positioned to extend through an inner bore GB of the graft G to secure the bone plate BP at the surgical site S. In other embodiments, the inner bore GB is omitted. The graft G is dimensioned to extend along a backside of the bone plate BP such that at least a portion of the graft G is spaced apart from a sidewall of the bone plate BP, as illustrated in FIG. 11.

The surgical site S may be prepared for receiving the graft G and at least a portion of the bone plate BP. This may include forming at least one recess BR in the bone B. The recess BR may be formed to remove tissue from a defect in the bone B. The recess BR can be dimensioned to at least partially receive the bone plate BP and graft G. The recess BR may be drilled, punched, reamed, tapped, or otherwise formed. The bone plate BP can be situated at the surgical site S such that the backside of the bone plate BP abuts against surfaces of the recess BR.

The bone hole BH is dimensioned to extend inwardly from a floor of the recess BR, as illustrated in FIG. 11. The bone hole BH is dimensioned to at least partially receive the anchoring member BP-M. The anchoring member BP-M can be screwed or press fit into the bone hole BH, for example, to secure the bone plate BP.

A head portion or glenosphere HP can be secured to the bone plate BP to provide an articulating surface for mating with an opposed articulating member M. The articulating member M can be an implant secured to the humerus, for example. In other embodiments, the bone plate BP provides the articulating surface.

The novel device and method of this disclosure provide versatility in preparing a surgical site. The disclosed drill assembly 20 can be utilized to form a bone hole or recess having various depths and dimensions. The drill assembly 20 includes one or more features that limit relative rotation and/or axial movement between the drill shaft 22 and depth collar 24, which can improve precision in setting and maintaining the selected depth of the bone hole or recess to be formed in the surgical site.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A drill assembly for preparation of a surgical site, comprising: a drill shaft including one or more cutting surfaces; a depth collar dimensioned to at least partially cover the one or more cutting surfaces, and the depth collar including a first set of teeth; a ratcheting sleeve including a second set of teeth, the second set of teeth dimensioned to mate with the first set of teeth to oppose relative rotation between the depth collar and the drill shaft; and wherein, when the first set of teeth and the second set of teeth are engaged together, the ratcheting sleeve limits movement of the depth collar.

2. The assembly as recited in claim 1, wherein:
the drill shaft includes an intermediate portion between a shank portion and a drill body portion, the drill body portion comprising the one or more cutting surfaces;
the depth collar includes first threading along a first passageway dimensioned to at least partially receive the intermediate portion; and
the intermediate portion includes second threading dimensioned to engage with the first threading such that relative rotation between the depth collar and the intermediate portion causes the depth collar to move along a longitudinal axis of the drill shaft.

3. The assembly as recited in claim 2, wherein the first set of teeth extend axially from a proximal end portion of the depth collar relative to the longitudinal axis, and the second set of teeth extend axially from a distal end portion of the ratcheting sleeve relative to the longitudinal axis.

4. The assembly as recited in claim 2, further comprising:
a spring member that biases the second set of teeth towards the first set of teeth.

5. The assembly as recited in claim 2, wherein the depth collar includes a viewing window at least partially axially aligned with the one or more cutting surfaces relative to the longitudinal axis.

6. The assembly as recited in claim 1, further comprising:
a spring member that biases the ratcheting sleeve towards the depth collar in an installed position.

7. The assembly as recited in claim 6, wherein:
the drill shaft includes an intermediate portion between a shank portion and a drill body portion, the drill body portion comprising the one or more cutting surfaces;
the intermediate portion includes a first shoulder;
the ratcheting sleeve includes a second passageway at least partially receiving the intermediate portion, and the ratchet sleeve includes a second shoulder along the second passageway; and
the spring member is compressible between the first shoulder and the second shoulder in response to moving the ratcheting sleeve in a direction away from the drill body portion.

8. The assembly as recited in claim 7, wherein the intermediate portion includes a slot, and further comprising:
a retention pin mechanically attached to the ratcheting sleeve such that the retention pin is at least partially received in the slot.

9. The assembly as recited in claim 8, wherein the retention pin extends inwardly from a sidewall of the ratcheting sleeve bounding the second passageway such that the retention pin limits relative rotation between the ratcheting sleeve and the drill shaft.

10. The assembly as recited in claim 9, wherein the drill shaft includes a shaft passageway extending along a longitudinal axis between the shank portion and the drill body portion such that the shaft passageway intersects the slot.

11. A drill assembly for preparation of a surgical site, comprising:
a drill shaft including one or more cutting surfaces;
a depth collar movable along the one or more cutting surfaces in response to relative rotation between the depth collar and the drill shaft, wherein the depth collar includes a distal end portion dimensioned to contact bone adjacent to the one or more cutting surfaces; and
a ratcheting sleeve moveable along the drill shaft between a first position and a second, different position relative to a longitudinal axis of the drill shaft, wherein the ratcheting sleeve is spaced apart from the depth collar in the first position and is engaged with the depth collar in the second position such that the ratcheting sleeve limits relative rotation between the depth collar and the drill shaft.

12. The assembly as recited in claim 11, wherein:
the depth collar includes a first set of teeth; and
the ratcheting sleeve includes a second set of teeth dimensioned to mate with the first set of teeth in the second position.

13. The assembly as recited in claim 11, further comprising a retention pin that limits relative rotation between the ratcheting sleeve and the drill shaft.

* * * * *

UNITED STATES PATENT AND TRADEMARK OFFICE
CERTIFICATE OF CORRECTION

| | |
|---|---|
| PATENT NO. | : 11,154,308 B2 |
| APPLICATION NO. | : 16/540144 |
| DATED | : October 26, 2021 |
| INVENTOR(S) | : Rudraksh Khosla et al. |

It is certified that error appears in the above-identified patent and that said Letters Patent is hereby corrected as shown below:

On the Title Page

Item (72) Inventors: Line 5-6; replace "Tyler Clevett," with --James Tyler Clevett,--

Signed and Sealed this
Twentieth Day of September, 2022

Katherine Kelly Vidal
*Director of the United States Patent and Trademark Office*